United States Patent
Dhainaut et al.

(10) Patent No.: US 6,562,953 B2
(45) Date of Patent: May 13, 2003

(54) PROCESS WHICH IS USEFUL FOR CONVERTING THE CARBONYL FUNCTION IN POSITION 4" OF THE CLADINOSE UNIT OF AN AZA-MACROLIDE INTO AN AMINE DERIVATIVE

(75) Inventors: Jildaz Dhainaut, Rigneux le Franc (FR); Patrick Leon, Tassin (FR); Frédéric Lhermitte, Saint-Symphorien-D'Ozon (FR); Gilles Oddon, Lyons (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/858,671

(22) Filed: May 16, 2001

(65) Prior Publication Data
US 2002/0013454 A1 Jan. 31, 2002

(30) Foreign Application Priority Data
May 30, 2000 (FR) .............................. 00 06942

(51) Int. Cl.$^7$ ................................................ C07H 1/00
(52) U.S. Cl. ...................... 536/7.4; 536/18.5
(58) Field of Search .................. 536/7.4, 18.5

(56) References Cited

U.S. PATENT DOCUMENTS
4,512,982 A * 4/1985 Hauske et al. ................ 514/29

FOREIGN PATENT DOCUMENTS
EP 0 508 699 A 10/1992

OTHER PUBLICATIONS
K. Shankaran et al., "Preparation and Activities of 4–EPI and 4–Deoxy–4–Amino Analogs Derived from 9–Deoxo–8A–AZA–8A–Homeorythromycin A", Bioorganic & Medicinal Chemistry Letters, GB, Oxford, vol. 4, No. 9, 1994, pp. 1111–1116.

* cited by examiner

Primary Examiner—Elli Peselev
(74) Attorney, Agent, or Firm—Frommer Lawrence & Haug, LLP; William S. Frommer; Thomas J. Kowalski

(57) ABSTRACT

The invention relates to a process for preparing compound of general formula I

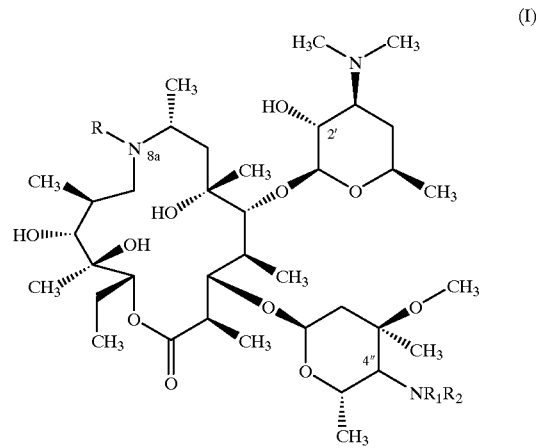

by reductive amination of the corresponding (4")-carbonyl derivative, characterized in that it comprises:
placing the said (4")-carbonyl derivative in contact with at least one nitrogenous reagent and a Lewis acid under conditions that are favourable for converting the 4" carbonyl function,
reducing the resulting mixture using a reducing agent, and
optionally deprotecting the hydroxyl function in position 2',
to give the expected compound of general formula I.

26 Claims, No Drawings

PROCESS WHICH IS USEFUL FOR CONVERTING THE CARBONYL FUNCTION IN POSITION 4" OF THE CLADINOSE UNIT OF AN AZA-MACROLIDE INTO AN AMINE DERIVATIVE

This application claims priority from U.S. application Ser. No. 60/219,513, filed Jul. 20, 2000 and French application Ser. No. 00 06942, filed May 30, 2000. Each of these applications and each document cited or referenced in each of these applications ("application cited documents"), and each document cited or referenced in application cited documents, are hereby incorporated herein by reference.

The present invention relates to a process which is useful in particular for converting the carbonyl function in position 4"of the cladinose unit of an aza-macrolide into an amine derivative.

The present invention relates more particularly to the field of erythromycin-type macrolide antibiotics and more particularly to the aza-macrolide derivatives thereof which form the subject of patent EP 508 699 and which correspond to the following general formula:

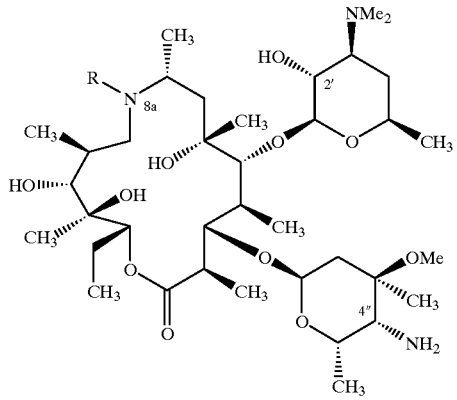

in which R represents a hydrogen atom or a $C_1$–$C_{10}$ alkyl, $C_2$–$C_{10}$ alkenyl or $C_6$–$C_{12}$ arylsulphonyl group, which may be substituted.

These compounds are obtained from erythromycin and their synthesis involves two major steps:
- the creation of the 8a-azalide macrocycle from the (Z) oxime which undergoes a stereospecific Beckmann rearrangement, and
- the modification of the cladinose group in position 4"which consists in converting the 4"(S)—OH into 4"(R)—$NH_2$, i.e. with inversion of configuration, which may be illustrated as follows:

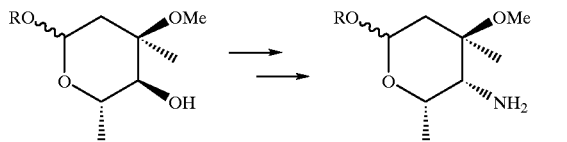

In point of fact, the route actually selected to carry out this conversion of the 4"(S)—OH function into 4"(R)—$NH_2$ is not entirely suitable for industrial-scale production.

It involves, successively, an oxidation of the hydroxyl function in position 4" into a ketone function and then conversion of this ketone into an oxime, which, on reduction, gives an approximately 1 to 1 mixture of the expected amine derivative and its 4" epimer. The isomers obtained after this synthetic route are obtained in a low yield of about 20% and in addition are difficult to separate by chromatography. Thus, for a crude reaction yield of about 20%, only about 7% of the amine derivative with inversion of configuration is obtained.

The subject of the present invention is, precisely, to propose a novel route of access to these derivatives aminated in position 4", in satisfactory yield.

More specifically, a subject of the present invention is described in the following numbered paragraphs:

1. Process for preparing a compound of general formula I

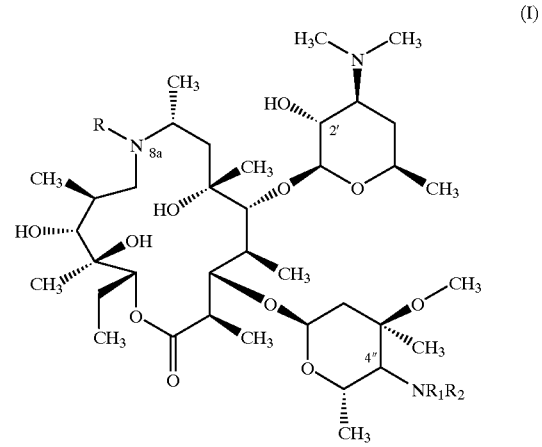

in which:
R is a hydrogen atom or an optionally substituted $C_1$–$C_{10}$ alkyl, $C_2$–$C_{10}$ alkenyl or $C_6$–$C_{12}$ arylsulphonyl group, and $R_1$ and $R_2$, which may be identical or different, represent a hydrogen atom, a $C_1$–$C_{10}$ alkyl group optionally substituted with one or more optionally substituted aryl groups, or an optionally substituted $C_6$–$C_{12}$ aryl group, by reductive amination of a compound of general formula II:

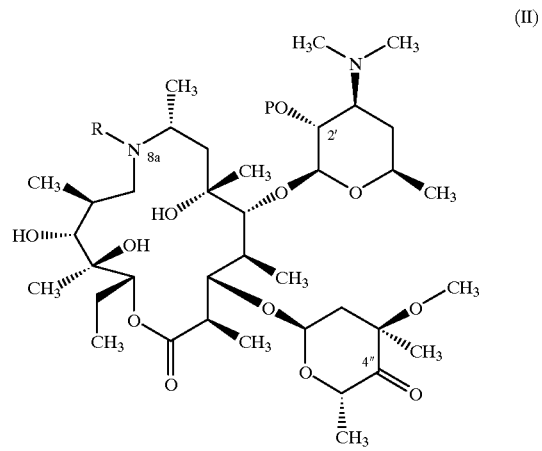

in which:
R is as defined in the general formula I, and
P represents a hydrogen atom or a protecting group, characterized in that it comprises:
  placing the said compound of general formula II in contact with at least one nitrogenous reagent and a Lewis acid under conditions that are favourable for converting the 4" carbonyl function,
  reducing the resulting mixture using a reducing agent, and
  optionally deprotecting the hydroxyl function in position 2', to give the expected compound of general formula I.

2. Process according to paragraph 1, characterized in that the compound of general formula I is obtained in the form of a mixture of its 2 isomers 4"R and 4"S.

3. Process according to paragraphs 1 or 2, characterized in that the 4"R isomer is obtained as the major product.

4. Process according to one of the preceding paragraphs, characterized in that the nitrogenous reagent is chosen from ammonia, ammonium salts, for instance ammonium acetate or ammonium hydrochloride, primary amines $NH_2R_A$, secondary amines $NH(R_A)_2$ with the radicals $R_A$, which may be identical or different, representing a $C_1$ to $C_{10}$ alkyl or $C_6$ to $C_{12}$ aryl group or a silyl group of the type $SiR_BR_CR_D$ in which the groups $R_B$, $R_C$ and $R_D$, which may be identical or different, can be an alkyl or aryl group.

5. Process according to paragraph 4, characterized in that the nitrogenous reagent is chosen from benzylamine, hexamethyldisilazane and ammonia.

6. Process according to one of the preceding paragraphs, characterized in that the nitrogenous reagent is introduced in a proportion of from 1 to 30 equivalents relative to the compound of general formula II and preferably in a proportion of from 1 to 10 equivalents.

7. Process according to one of the preceding paragraphs, characterized in that the Lewis acid is aprotic.

8. Process according to one of the preceding paragraphs, characterized in that the Lewis acid is introduced in a proportion of from 1 to 30 equivalents relative to the compound of general formula II.

9. Process according to one of the preceding paragraphs, characterized in that the Lewis acid is chosen from organometallic complexes of the elements from column IVB, IIIA or IIB of the Periodic Table of the Elements.

10. Process according to paragraph 9, characterized in that the said complex is chosen from titanium(IV) isopropoxide, aluminium(III) isopropoxide, titanium(IV) isopropoxide bis(acetylacetonate) and zinc(II) trifluoroacetate.

11. Process according to one of the preceding paragraphs, characterized in that the reducing agent is a metal hydride.

12. Process according to paragraph 11, characterized in that it is a boron or aluminium hydride.

13. Process according to paragraph 11 or 12, characterized in that it is sodium, lithium or zinc borohydride.

14. Process according to any one of the preceding paragraphs, characterized in that it is used in the presence of an organic solvent chosen from aromatic hydrocarbons, in particular toluene, halogenated solvents such as dichloromethane, alcohols such as methanol, nitriles such as acetonitrile, ethers such as THF or sulphoxides such as DMSO.

15. Process according to any one of the preceding paragraphs, characterized in that the Lewis acid is titanium isopropoxide or aluminium isopropoxide, the nitrogenous reagent is ammonia, hexamethyldisilazane or benzylamine, and the solvent is dichloromethane, tetrahydrofuran or toluene.

16. Process according to paragraph 15, characterized in that the reducing agent is sodium borohydride or lithium borohydride.

17. Process according to any one of the preceding paragraphs, characterized in that the compound of formula II dissolved in an organic solvent is added to the mixture of the Lewis acid and the nitrogenous reagent.

18. Process according to any one of paragraphs 1 to 16, characterized in that the compound of formula II and the Lewis acid are mixed together in an organic solvent and the nitrogenous reagent is added slowly to this mixture.

19. Process according to any one of paragraphs 1 to 16, characterized in that the compound of formula II is mixed with the nitrogenous reagent in an organic solvent and the Lewis acid is then added.

After the said process, the two isomeric forms R and Z of the expected 4" amine derivative are obtained. However, the diastereoselectivity is such that the 4"R form is generally obtained predominantly. As emerges from the examples given below, the process claimed can advantageously give a 4"R/4"S mixture with a molar ratio from 60/40 and which may be up to 90/10.

Consequently, the process claimed is found to be particularly advantageous for obtaining this (4"R)-amino derivative, whose separation from the (4"S)-amino form obtained as the minor product can then be carried out by the techniques known to those skilled in the art.

In the context of the present invention, a compound of general formula II is thus reacted with a nitrogenous agent and a Lewis acid under conditions that are sufficient to allow the conversion of the carbonyl function in position 4". When this conversion is complete, the resulting mixture is reduced directly to give the compound of general formula I.

The process claimed advantageously does not require an intermediate step and allows the two reactions to be carried out in sequence in the same reaction medium.

Nitrogenous reagents which can be used in particular include a compound chosen from ammonia, ammonium salts such as ammonium acetate, ammonium hydrochloride, primary amines $NH_2R_A$ and secondary amines $NH(R_A)_2$ in which the radicals $R_A$, which may be identical or different, represent a $C_1$ to $C_{10}$ alkyl or $C_6$ to $C_{12}$ aryl group or a silyl group of the type $SiR_BR_CR_D$ in which the groups $R_B$, $R_C$ and $R_D$, which may be identical or different, can be an alkyl or aryl group.

Benzylamine, ammonia and hexamethyldisilazane are most particularly suitable for the invention.

The nitrogenous reagent can be used in a proportion of from 1 to 30 equivalents relative to the compound of general formula II and preferably in a proportion of from 1 to 10 equivalents.

As regards the Lewis acid, it is preferably aprotic.

Lewis acids which are most particularly suitable include organometallic complexes of the elements from column IVB, IIIA or IIB of the Periodic Table of the Elements, and in particular those based on titanium, zinc and aluminium. The substituents on these complexes can be of alkoxy, acyloxy, sulphonate, halo, Schiff's base or acetylacetonate type or a n-donor ligand such as cyclopentadienyl.

The following compounds are thus suitable for the invention: titanium(IV) isopropoxide, aluminium(III) isopropoxide, titanium(IV) isopropoxide bis(acetylacetonate), zinc(II) trifluoroacetate.

This Lewis acid can thus be used in a proportion of from 1 to 30 equivalents relative to the compound of general formula II and more preferably in a proportion of from 1 to 10 equivalents.

As discussed previously, the Lewis acid and the nitrogenous reagents are, in a first step, placed in contact with the compound of general formula II.

It is thus possible to react:
the Lewis acid and the compound of general formula II before introducing the nitrogenous reagent,
the Lewis acid and the nitrogenous reagent, followed by the compound of general formula II, or
the nitrogenous reagent, the compound of general formula II and the Lewis acid simultaneously.

Irrespective of the order selected for placing the reagents in contact, the reducing agent is added only once the conversion of the 4" ketone function is complete.

Advantageously, the reaction medium is then reduced directly using a reducing agent.

Metal hydrides are most particularly suitable in the invention as reducing agent. Preferably, it is an aluminium or boron hydride and more preferably a substituted or unsubstituted boron hydride.

Substituted borohydrides which may thus be used are borohydrides mono-, di- or trisubstituted with:
mono- or dicarboxylic acids such as RCO$_2$H in which R represents an optionally substituted alkyl or aryl group,
alcohols of the type ROH in which R is as defined above, or
1,2-, 1,3- or 1,4-diols and associated with a countercation, which is either of alkaline nature such as Li, Na or K, or of organic nature of quaternary ammonium type or alternatively of metallic type such as zinc, calcium or zirconium.

According to a preferred embodiment, the borohydride agent is different from a cyanoborohydride derivative.

Sodium, lithium and zinc borohydrides or sodium dibenzoyloxyborohydride are most particularly suitable for the invention.

The reducing agent is used in an amount which is sufficient to form the compound of general formula III:

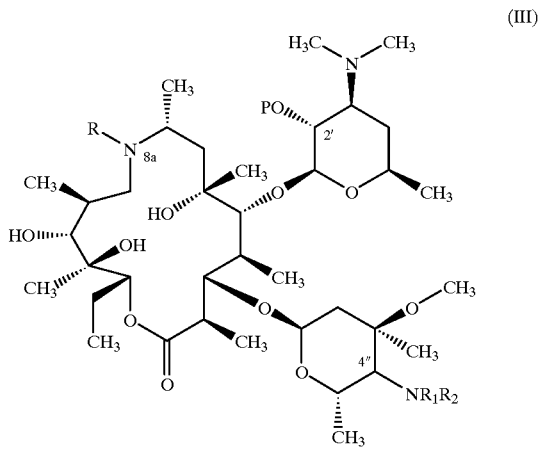

(III)

Generally, the amount used ranges from 1 to 10 equivalents and more preferably from 1 to 5 equivalents.

The entire process is generally carried out in an organic solvent.

This solvent can be chosen in particular from aromatic hydrocarbons such as toluene, halogenated solvents such as dichloromethane, alcohols such as methanol, nitriles such as acetonitrile, ethers such as THF and sulphoxides such as DMSO.

As regards the other reaction parameters, i.e. reaction temperature and reaction time, their adjustment falls within the competence of a person skilled in the art. The reaction can thus be carried out at a temperature of between −30° C. and the reflux point of the solvent and this reaction temperature can vary in the course of the reaction.

As regards the compound of general formula II, it is generally obtained beforehand starting from the compound of general formula IV:

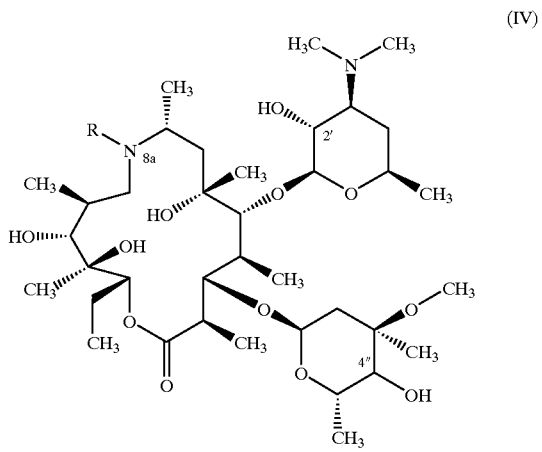

(IV)

by protecting the hydroxyl function in position 2' of the said compound, followed by oxidation of the hydroxyl function in position 4".

The protection is carried out conventionally using a conventional protecting group for a hydroxyl function, such as those featured in "Protective groups in organic synthesis" Second Edition, Theodora W. Greene, P. G. Wuts, Wiley Intersciences, pp. 10–142. The procedures for carrying out the protection and deprotection operations are also described in the book referred to above.

As regards the oxidation, it can be carried out according to the procedure described in EP 508 699.

After the reduction according to the process claimed, deprotection of the function at 2' is thus carried out, if necessary.

According to preferred variants of the invention, titanium isopropoxide or aluminium isopropoxide is used as Lewis acid. As regards the associated nitrogenous reagent, it is preferably chosen from ammonia, hexamethyldisilazane and benzylamine. Under these conditions, the solvent used is preferably chosen from dichloromethane, tetrahydrofuran and toluene.

The preferred reducing agent is sodium borohydride or lithium borohydride.

According to a first variant of the invention, the compound of the formula II dissolved in an organic solvent, preferably toluene or dichloromethane, is added to a mixture of the Lewis acid such as titanium(IV) isopropoxide or aluminium(III) isopropoxide with the nitrogenous reagent, such as benzylamine, hexamethyldisilazane or ammonia, and the assembly is kept stirring at room temperature and optionally heated to the reflux point of the reaction medium.

In a second variant, the Lewis acid, such as titanium(IV) isopropoxide is placed in contact with the compound of formula II in an organic solvent such as THF or toluene, followed by slow addition of the nitrogenous reagent, preferably hexamethyldisilazane. The assembly is kept stirring at room temperature and optionally heated to the reflux point of the reaction medium.

According to a third variant, the compound of general formula II is mixed with the nitrogenous reagents, preferably ammonia, in an organic solvent. The Lewis acid, preferably titanium diisopropoxide bis(acetylacetonate) dissolved in the same organic solvent, is then added thereto and the assembly is kept stirring at room temperature and optionally heated to the reflux point of the reaction medium.

Irrespective of the variant considered, the reduction is carried out consecutively by adding the reducing agent directly into the reaction medium. The reduction is allowed to go to completion, followed by hydrolysis of the reaction medium and then at least one extraction.

If necessary, the compound of general formula III is then deprotected so as to obtain the compound of general formula I, which is then isolated according to a conventional procedure which generally involves extraction, washing and then drying operations.

The examples given below are presented by way of non-limiting illustration of the present invention.

EXAMPLE 1

Synthesis of 2'-O-acetyl-4"-deoxy-4"-N-benzylamino-9-deoxo-8a-aza-8a-methyl-8a-homoerythromycin A A solution of titanium(IV) isopropoxide (0.3 ml, 1 mmol, 8 equiv.) and benzylamine (100 mg, 0.93 mmol, 7.4 equiv.) is stirred for 1 h at room temperature. A solution of 2'-O-acetyl-4"-deoxy-4"-oxo-9-deoxo-8a-aza-8a-methyl-8a-homoerythromycin A (100 mg, 0.12 mmol) in THF (0.5 ml) is added. The reaction mixture is stirred at room temperature for 96 h and a 2M solution of lithium borohydride in THF (0.25 ml, 0.5 mmol, 4 equiv.) is then added. After reaction for 2 h, the reaction medium is hydrolyzed by addition of methanol and is then diluted with ethyl acetate and washed with aqueous hydrochloric acid solution pH=3 (10 ml). The aqueous phase is separated out and basified to pH=10 with sodium hydroxide, and extracted with ethyl acetate (2×20 ml). The combined organic phases are dried over sodium sulphate and evaporated. NMR analysis indicates the formation of 4"-deoxy-4"(R)-N-benzylamino-9-deoxo-8a-aza-8a-methyl-8a-homoerythromycin A as the major product.

EXAMPLE 2

Synthesis of 4"-deoxy-4"-(R)-amino-9-deoxo-8a-aza-8a-methyl-8a-homoerythromycin A 2.1/ with the Ti(Oi-Pr)$_4$/HMDS/LiBH$_4$ system:

A solution of titanium(IV) isopropoxide (7.5 ml, 25.4 mmol, 4 equiv.) and hexamethyldisilazane (10.5 ml, 50 mmol, 8 equiv.) is stirred for 5 h at room temperature. A solution of 2'-O-acetyl-4"-deoxy-4"-oxo-9-deoxo-8a-aza-8a-methyl-8a-homoerythromycin A (5 g, titre=69% w/w, 4.4 mmol) in toluene (20 ml) is then added and the mixture is stirred for 4 h at room temperature and then for 20 h at 70° C. After cooling to room temperature, a 10% solution of lithium borohydride in THF (5 ml, 22.9 mmol, 3.6 equiv.) diluted in toluene (15 ml) is added. After reaction for 2 h, methanol is added and the medium is then diluted with ethyl acetate and poured into water (50 ml). The aqueous phase is acidified to pH=2–3 and then separated out after extraction and basified to pH=10 by addition of sodium hydroxide. After extraction with ethyl acetate (2×60 ml), the combined organic phases are dried over sodium sulphate and evaporated (4.27 g). The crude product is taken up in methanol (30 ml) and this solution is heated for 24 h at 45° C. After evaporation of the methanol, HPLC analysis indicates a (4"R)/(4"S) ratio=73/27 and a yield of 41% for the (4"R)-amino derivative.

2.2/ with the Ti(Oi-Pr)$_4$/HMDS/NaBH$_4$ system:

A solution of titanium(IV) isopropoxide (3.75 ml, 12.7 mmol, 2.9 equiv.) and 2'-O-acetyl-4"-deoxy-4"-oxo-9-deoxo-8a-aza-8a-methyl-8a-homoerythro-mycin A (5 g, titre=69% w/w, 4.4 mmol) in THF (15 ml) is stirred for 5 h at room temperature. Hexamethyl-disilazane (5.25 ml, 24.9 mmol, 5.6 equiv.) is added slowly at room temperature. The reaction mixture is then heated for 20 h at 55° C. After cooling to room temperature, sodium borohydride (1 g, 26.4 mmol, 6 equiv.) is added portionwise. After stirring for 18 h, the reaction mixture is poured into water pH=3 (50 ml) and ethyl acetate (20 ml). After extraction, the aqueous phase is separated out, basified to pH=10 and extracted with ethyl acetate (2×50 ml). The combined organic phases are dried over sodium sulphate and evaporated (4.44 g). The crude product is taken up in methanol (30 ml) and this solution is heated for 24 h at 45° C. After evaporation of the methanol, HPLC analysis indicates a (4"R)/(4"S) ratio=76/24 and a yield of 60% for the (4"R)-amino derivative.

2.3/ with the Al(Oi-Pr)$_3$/NH$_3$/LiBH$_4$ system:

Ammonia is bubbled for 10 min into a solution of aluminium(III) isopropoxide (1 g, 4.9 mmol, 3.9 equiv.) in toluene (2 ml). A solution of and 2'-O-acetyl-4"-deoxy-4"-oxo-9-deoxo-8a-aza-8a-methyl-8a-homoerythromycin A (0.500 g, 0.63 mmol) in toluene (0.6 ml) is then added. After stirring for 42 h at room temperature, the reaction mixture is cooled to 0° C. and a 2M solution of lithium borohydride in THF (1.27 ml, 2.5 mmol, 4 equiv.) is then added. After stirring for 5 h, methanol is added and the medium is then diluted with ethyl acetate and poured into water (30 ml). The aqueous phase is acidified to pH=2–3 and then separated out after extraction and basified to pH=10 by addition of sodium hydroxide. After extraction with ethyl acetate (2×40 ml), the combined organic phases are dried over sodium sulphate and evaporated. The crude product is taken up in methanol (10 ml) and this solution is heated for 24 h at 45° C. After evaporation of the methanol (0.382 g), HPLC analysis indicates a (4"R)/(4"S) ratio=88/12 and a yield of 56% for the (4"R)-amino derivative.

2.4/ with the Ti(Oi-Pr)$_4$/NH$_3$/LiBH$_4$ system:

Ammonia is bubbled for 30 min into a solution of titanium(IV) isopropoxide (1.5 ml, 5.1 mmol, 4 equiv.). This mixture is then transferred into a solution of 2'-O-acetyl-4"-deoxy-4"-oxo-9-deoxo-8a-aza-8a-methyl-8a-homoerythromycin A (1 g, titre=72% w/w, 0.9 mmol) in dichloromethane (1 ml). After stirring for 24 h at room temperature, a 10% solution (in THF) of lithium borohydride (0.93 g, 5 mmol, 4 equiv.) diluted with THF (1 ml) is added. After stirring for 2 h, methanol is added and the medium is then diluted with ethyl acetate and poured into water (30 ml). The aqueous phase is acidified to pH=2–3 and then separated out after extraction and basified to pH=10 by addition of sodium hydroxide. After extraction with ethyl acetate (2×40 ml), the combined organic phases are dried over sodium sulphate and evaporated (0.96 g). The crude product is taken up in methanol (10 ml) and this solution is heated for 24 h at 45° C. After evaporation of the methanol, HPLC analysis indicates a (4"R)/(4"S) ratio=72/38 and a yield of 73% for the (4"R)-amino derivative.

2.5/ with the Ti(acac)$_2$ (Oi-Pr)$_2$/NH$_3$/LiBH$_4$ system:

4"-Deoxy-4"-oxo-9-deoxo-8a-aza-8a-methyl-8a-homoerythromycin A (100 mg, 0.13 mmol) is dissolved in a 2N solution of ammonia in isopropanol (0.27 ml). A 75% solution of titanium diisopropoxide bis(acetylaacetonate) in isopropanol (0.13 ml, 0.27 mmol, 2 equiv.) is then added. After stirring for 20 h at room temperature, a 2M solution of lithium borohydride in THF (0.27 ml, 0.53 mmol, 4 equiv.) is added. After reaction for 1.5 h, methanol is added and the medium is then diluted with ethyl acetate and poured into water (20 ml). The aqueous phase is acidified to pH=2–3 and then separated out after extraction and basified to pH=10 by addition of sodium hydroxide. After extraction with ethyl acetate (2×15 ml), the combined organic phases are dried over sodium sulphate and evaporated. HPLC analysis indicates a (4"R)/(4"S) ratio=61/39.

2.6/ with the $Zn(OCOCF_3)_2$/HMDS/$NaBH_4$ system:

A mixture of 2'-O-acetyl-4"-deoxy-4"-oxo-9-deoxo-8a-aza-8a-methyl-8a-homoerythromycin A (100 mg, 0.13 mmol), zinc trifluoroacetate (43 mg, 1.4 mmol, 1.15 equiv.) and hexamethyldisilazane (0.2 ml, 0.9 mmol, 7 equiv.) in ethyl acetate is heated for 13 h at 60° C. After cooling to room temperature, sodium borohydride (20 mg, 0.53 mmol, 4 equiv.) is added. After stirring for 18 h, the medium is diluted with methanol and stirred for 24 h at room temperature. The medium is then diluted with ethyl acetate (10 ml) and poured into water (20 ml). The aqueous phase is acidified to pH=2–3 and then separated out after extraction and basified to pH=10 by addition of sodium hydroxide. After extraction with ethyl acetate (2×15 ml), the combined organic phases are dried over sodium sulphate and evaporated. HPLC analysis indicates a (4"R)/(4"S) ratio=50/50.

2.7/ with the $Ti(Oi-Pr)_4$/HMDS/$(PhCO_2)_2BH_2Na$ system:

Hexamethyldisilazane (0.5 ml, 2.4 mmol, 9.3 equiv.) and titanium(IV) isopropoxide (0.12 ml, 0.41 mmol, 1.6 equiv.) are successively added at room temperature to a solution of 2'-O-acetyl-4"-deoxy-4"-oxo-9-deoxo-8a-aza-8a-methyl-8a-homoerythromycin A (200 mg, 0.25 mmol) in acetonitrile (2 ml). After stirring for 48 h at room temperature, a suspension of sodium dibenzoyloxyborohydride (10 equiv.) (prepared by reaction between 1 equiv. of sodium borohydride and 2 equiv. of benzoic acid) in THF (1 ml) is added. After stirring for 18 h at room temperature, the medium is then diluted with ethyl acetate (10 ml) and poured into water (20 ml). The aqueous phase is acidified to pH=2–3 and then separated after extraction and basified to pH=10 by addition of sodium hydroxide. After extraction with ethyl acetate (2×15 ml), the combined organic phases are dried over sodium sulphate and evaporated. HPLC analysis indicates a (4"R)/(4"S) ratio=73/27.

2.8/ with the $Ti(Oi-PR)_4$/HMDS/$Zn(BH_4)_2$ system:

Hexamethyldisilazane (0.25 ml, 1.2 mmol, 9.3 equiv.) and titanium(IV) isopropoxide (60 µl, 0.20 mmol, 1.6 equiv.) are successively added at room temperature to a solution of 2'-O-acetyl-4"-deoxy-4"-oxo-8a-aza-8a-methyl-8a-homoerythromycin A (100 mg, 0.13 mmol) in acetonitrile (1 ml). After stirring for 48 h at room temperature, zinc borohydride (8 equiv.) is added. After stirring for 18 h at room temperature, the medium is then diluted with ethyl acetate (10 ml) and poured into water (20 ml). The aqueous phase is acidified to pH=2–3 and then separated out after extraction and basified to pH=10 by addition of sodium hydroxide. After extraction with ethyl acetate (2×15 ml), the combined organic phases are dried over sodium sulphate and evaporated. HPLC analysis indicates a (4"R)/(4"S) ratio=73/27.

2.9/ with the $Ti(Oi-PR)_4$/HMDS/n-pent$OBH_3Na$ system:

Hexamethyldisilazane (0.25 ml, 1.2 mmol, 9.3 equiv.) and titanium(IV) isopropoxide (60 µl, 0.20 mmol, 1.6 equiv.) are successively added at room temperature to a solution of 2'-O-acetyl-4"-deoxy-4"-oxo-8a-aza-8a-methyl-8a-homoerythromycin A (100 mg, 0.13 mmol) in acetonitrile (1 ml). After stirring for 48 h at room temperature, sodium n-pentoxyborohydride (9 equiv.; prepared by reaction between 1 equiv. of sodium borohydride and 1 equiv. of n-pentanol) is added. After stirring for 18 h at room temperature, the medium is then diluted with ethyl acetate (10 ml) and poured into water (20 ml). The aqueous phase is acidified to pH=2–3 and then separated out after extraction and basified to pH=10 by addition of sodium hydroxide. After extraction with ethyl acetate (2×15 ml), the combined organic phases are dried over sodium sulphate and evaporated. HPLC analysis indicates a (4"R)/(4"S) ratio=63/37.

2.10/ with the $Ti(Oi-PR)_4$/HMDS/$LiBH_4$ system:

A solution of titanium(IV) isopropoxide (0.15 ml, 0.5 mmol, 4 equiv.) and hexamethyldisilazane (0.11 ml, 0.5 mmol, 4 equiv.) is stirred for 1 h at room temperature. 2'-O-Acetyl-4"-deoxy-4"-oxo-9-deoxo-8a-aza-8a-methyl-8a-homoerythromycin A (0.100 g, 0.13 mmol) is then added and this solution is stirred for 18 h at room temperature. A 2M solution of lithium borohydride in THF (0.25 ml, 0.5 mmol, 4 equiv.) is added. After reaction for 4 h, methanol is added and the medium is then diluted with ethyl acetate and poured into water (10 ml). The aqueous phase is acidified to pH=2–3 and then separated out after extraction and basified to pH=10 by addition of sodium hydroxide. After extraction with ethyl acetate (2×20 ml), the combined organic phases are dried over sodium sulphate and evaporated. The crude product is taken up in methanol (10 ml) and this solution is heated for 24 h at 45° C. After evaporation of the methanol, HPLC analysis indicates a (4"R)/(4"S) ratio 91/9.

What is claimed is:

1. A process for preparing a compound of formula I

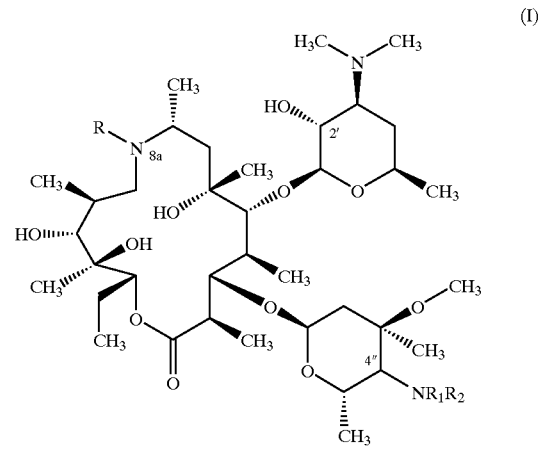

in which:
R is a hydrogen atom or an optionally substituted $C_1$–$C_{10}$ alkyl, $C_2$–$C_{10}$ alkenyl or $C_6$–$C_{12}$ arylsulphonyl group, and
$R_1$ and $R_2$, which may be identical or different, represent
a hydrogen atom, or
a $C_1$–$C_{10}$ alkyl group optionally substituted with one or more optionally substituted aryl groups, or an optionally substituted $C_6$–$C_{12}$ aryl group, said process comprising a reductive amination of a compound of formula II:

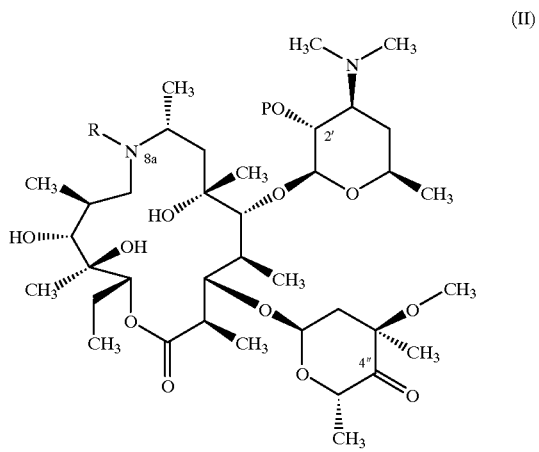

in which:
R is as defined in the formula I, and
P represents a hydrogen atom or a protecting group,
wherein said reductive amination comprises:
contacting the compound of formula II with at least one nitrogenous reagent and an aprotic Lewis acid to form a reaction medium, and,
reducing the reaction medium using a reducing agent,
whereby the contacting and reducing are under conditions that are favorable for converting the 4" carbonyl function of the compound of formula II to the 4" $NR_1R_2$ group of the compound of formula I.

2. The process according to claim 1, wherein P is a protecting group and the process further comprises deprotecting the hydroxyl function in position 2'.

3. The process according to claim 1, wherein the compound of formula I is obtained in the form of a mixture of its two isomers 4"R and 4"S.

4. The process according to claim 1, wherein the 4"R isomer is obtained as the major product.

5. The process according to claim 1, wherein the nitrogenous reagent is selected from the group consisting of ammonia, ammonium salt, primary amine $NH_2R_A$, and secondary amine $NH(R_A)_2$, wherein the radical $R_A$ which may be identical or different in the secondary amine, represents a $C_1$ to $C_{10}$ alkyl, or $C_6$ to $C_{12}$ aryl group, or a silyl group of the type $SiR_BR_CR_D$ in which the groups $R_B$, $R_C$ and $R_D$, which may be identical or different, represent an alkyl or aryl group.

6. The process according to claim 5, wherein the nitrogenous reagent is selected from the group consisting of benzylamine, hexamethyldisilazane and ammonia.

7. The process according to claim 5, wherein the ammonium salt is ammonium acetate or ammonium hydrochloride.

8. The process according to claim 1, wherein the nitrogenous reagent is introduced in a proportion of from 1 to 30 equivalents relative to the compound of formula II.

9. The process according to claim 8, wherein the nitrogenous reagent is introduced in a proportion of from 1 to 10 equivalents relative to the compound of formula II.

10. The process according to claim 1, wherein the Lewis acid is introduced in a proportion of from 1 to 30 equivalents relative to the compound of formula II.

11. The process according to claim 1, wherein the Lewis acid is an organometallic complex wherein to metal of the organometallic complex is an element from column IVB, IIIA or IIB of the Periodic Table of the Elements.

12. The process according to claim 11, wherein the metal of the organometallic complex is titanium, zinc or aluminum.

13. The process according to claim 12, wherein the organometallic complex is selected from the group consisting of titanium(IV) isopropoxide, aluminium(III) isopropoxide, titanium(IV) isopropoxide bis (acetylacetoflate) and zinc(II) trifluoroacetate.

14. The process according to claim 1, wherein the reducing agent is a metal hydride.

15. The process according to claim 14, wherein the reducing agent is a boron or aluminium hydride.

16. The process according to claim 14, wherein the reducing agent is sodium, lithium or zinc borohydride.

17. The process according to claim 1, wherein the process is performed in the presence of an organic solvent selected from the group consisting of an aromatic hydrocarbon, a halogenated organic solvent, an alcohol, a nitrile, an ether and a sulphoxide.

18. The process according to claim 17, wherein the organic solvent is toluene, dichloromethane, methanol, acetonitrile, tetrahydrofuran or DMSO.

19. The process according to claim 18, wherein the Lewis acid is titanium isopropoxide or aluminium isopropoxide, the nitrogenous reagent is ammonia, hexamethyldisilazane or benzylamine, and the solvent is dichloromethane, tetrahydrofuran or toluene.

20. The process according to claim 19, wherein the reducing agent is sodium borohydride or lithium borohydride.

21. The process according to claim 1 wherein the contacting step comprises adding the compound of formula II to a mixture of the Lewis acid and the nitrogenous reagent.

22. The process according to claim 21, wherein the contacting step comprises adding the compound of formula II dissolved in an organic solvent to the mixture of the Lewis acid and the nitrogenous reagent.

23. The process according to claim 1, wherein the contacting step comprises mixing the compound of formula II and the Lewis acid to form a mixture, and adding the nitrogenous reagent to the mixture.

24. The process according to claim 23, wherein the contacting step comprises mixing the compound of formula II and the Lewis acid together in an organic solvent to form the mixture, and adding the nitrogenous reagent slowly to the mixture.

25. The process according to claim 1, wherein the contacting step comprises mixing the compound of formula II and the nitrogenous reagent to form a mixture, and adding the Lewis acid to the mixture.

26. The process according to claim 25, wherein the contacting stop comprises mixing the compound of formula II is with the nitrogenous reagent in an organic solvent to form the mixture, and adding the Lewis acid to the mixture.

* * * * *